United States Patent
Kumazawa et al.

(10) Patent No.: US 9,681,943 B2
(45) Date of Patent: Jun. 20, 2017

(54) INTRAOCULAR LENS

(71) Applicant: KOWA COMPANY, LTD., Nagoya-shi, Aichi (JP)

(72) Inventors: Yutaka Kumazawa, Nagoya (JP); Kotaro Sakanishi, Komaki (JP); Atsushi Kobayashi, Nagoya (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 14/913,075

(22) PCT Filed: Sep. 2, 2014

(86) PCT No.: PCT/JP2014/073050
§ 371 (c)(1),
(2) Date: Feb. 19, 2016

(87) PCT Pub. No.: WO2015/033924
PCT Pub. Date: Mar. 12, 2015

(65) Prior Publication Data
US 2016/0166379 A1  Jun. 16, 2016

(30) Foreign Application Priority Data
Sep. 5, 2013  (JP) .................. 2013-184384

(51) Int. Cl.
*A61F 2/16* (2006.01)

(52) U.S. Cl.
CPC .............. *A61F 2/16* (2013.01); *A61F 2/1613* (2013.01); *A61F 2002/169* (2015.04); *A61F 2002/16901* (2015.04)

(58) Field of Classification Search
CPC .. A61F 2/16; A61F 2/1613; A61F 2002/1681; A61F 2002/169; A61F 2002/16901
See application file for complete search history.

(56) References Cited

U.S. PATENT DOCUMENTS 6,558,419 B1  5/2003 Pham et al.
2011/0130832 A1  6/2011 Shoji et al.

FOREIGN PATENT DOCUMENTS

EP  1493405 A1  1/2005
EP  2204143 A1  7/2010
(Continued)

OTHER PUBLICATIONS

Sep. 30, 2014 International Search Report issued in International Patent Application No. PCT/JP2014/073050.
(Continued)

*Primary Examiner* — Howie Matthews
(74) *Attorney, Agent, or Firm* — Oliff PLC

(57) ABSTRACT

An intraocular lens wherein an outer edge of a support part has a curved concave shape at a base thereof and extends therefrom toward a tip thereof with a curved convex shape having a radius of curvature of 5.25 to 7.50 mm. In a region where a Y coordinate of an orthogonal coordinate system is 1.0 mm or greater, an origin of the coordinate system being a geometric center of an optical part, an inner edge of the support part is positioned between shapes obtained by offsetting the outer edge of the support part by 0.2 mm and by 1.0 mm towards the X-axis origin. The tip of the support part is positioned in a region where the Y coordinate is greater than a radius of the optical part, outside a circle with a radius of 5.0 mm centered on the origin.

7 Claims, 4 Drawing Sheets
(1 of 4 Drawing Sheet(s) Filed in Color)

(56) References Cited

FOREIGN PATENT DOCUMENTS

| | | |
|---|---|---|
| JP | 3447764 B2 | 9/2003 |
| JP | 2005-021275 A | 1/2005 |
| JP | 2005-507742 A | 3/2005 |
| JP | 2010-158304 A | 7/2010 |
| JP | 2013-094406 A | 5/2013 |
| JP | 2013-523259 A | 6/2013 |

OTHER PUBLICATIONS

Apr. 3, 2017 Search Report issued in European Patent Application No. 14841874.2.

INTRAOCULAR LENS

TECHNICAL FIELD

The present invention relates to an intraocular lens that is used by being implanted in the human eye, for which an optical part and a support part are integrally formed using a soft material.

BACKGROUND ART

An intraocular lens used by being implanted in the human eye with the goal of supplementing or substituting the function of the crystalline lens or the like of the human eye such as of a cataract patient or the like is known from the past. For example, the item disclosed in Japanese Unexamined Patent Publication No. JP-A-2005-021275 (Patent Document 1) is such an item, and has a structure including a roughly disc shaped optical part implanted within the eye and arranged on an optical path within the eyeball, and a plurality of support parts provided to the optical part and extending to the outer circumference side.

For this kind of intraocular lens, the support parts press against the equator part of the lens capsule from the inside and is projected and stretched in the radial direction so as to be positioned in order to stably hold the optical part at the center within the lens capsule. Therefore, with a single-piece intraocular lens that is a foldable type with the optical part and support part integrally formed with a bendably deformable soft material, which is currently the mainstream, it is necessary to make up for the material strength being low, and to ensure a positioning effect using the support part.

In light of that, with the conventional single-piece intraocular lens, it was necessary to make the width dimension and thickness dimension large to increase the strength of the support part. In addition, as is noted in Patent Document 1, it is preferable to use an elbow design for which at an inner circumference side edge part of the support part, the base end part has a narrow width so as to hollow out a small diameter arc, and which swells in convex form adjacent to the tip side. With this elbow design, by concentrating stress and distortion at the base end part of the support part which has a narrow width, it is said that it is possible to inhibit biasing or inclining of the optical part due to buckling deformation of the tip side of the support part, as well as to reduce deformation due to stress transmission to the optical part.

Meanwhile, with intraocular lenses, post-surgery secondary cataracts are a significant problem. These secondary cataracts are a result of crystalline lens epithelial cells wrapping around to the rear surface of the intraocular lens and propagating after surgery, and vision becomes significantly worse due to the posterior capsule of the intraocular lens back side becoming turbid.

With the goal of inhibiting such secondary cataracts, for example in PCT Japanese Translation Patent Publication JP-A-2005-507742 (Patent Document 2), it is also proposed to prevent the crystalline lens epithelial cells from wrapping around to the lens rear surface by pressing an outer circumference edge part of an optical part rear surface as a sharp edge cross section against the posterior capsule. However, there are problems such as that the edge cross section brings on thickening of the optical part outer circumference, and when the intraocular lens is inserted into the capsule, it is difficult to induce curve deformation of the lens so as to be sufficiently small and the like, and it was difficult to obtain a sufficient secondary cataract inhibitory effect simply by giving an edge cross section.

In particular, when investigated by the inventors of the present invention, with a single-piece intraocular lens made of a soft material whereby the width dimension or thickness dimension of the support part is made large, or an elbow design is used having at the inner circumference side edge part of the support part, the base end part with a narrow width part hollowed in a small diameter arc state or a part swelling in a convex shape, it was discovered that inhibiting the risk of occurrence of a secondary cataract tends to be even more difficult.

BACKGROUND ART DOCUMENT

Patent Document

Patent Document 1: JP-A-2005-021275
Patent Document 2: JP-A-2005-507742

SUMMARY OF THE INVENTION

Problem the Invention Attempts to Solve

The present invention has been developed in view of the above-described matters as the background, and it is an object of the present invention to provide a single-piece intraocular lens with a novel structure which is able to obtain an inhibitory effect on secondary cataracts based on novel technological aspects.

Means for Solving the Problem

The first mode of the present invention provides an intraocular lens including: an optical part formed of a bendably deformable soft material; and a support part integrally provided to the optical part, the support part extending from the optical part toward an outer circumference side while inclining in a circumference direction, the intraocular lens being characterized in that: an outer circumference side edge part of the support part has a curved concave shape at a base part thereof, and has a curved convex shape with a radius of curvature of 5.25 to 7.50 mm at a portion further to a tip side thereof than the base part; an inner circumference side edge part of the support part has a curved concave shape at a base part thereof, and with an orthogonal coordinate system for which a geometric center of the optical part is an origin point, a tangent line to the base part of the inner circumference side edge part is an X axis, and an orthogonal line to the X axis is a Y axis, in a region where a Y coordinate value is 1.0 mm or greater, the inner circumference side edge part of the support part is positioned between a shape such that the outer circumference side edge part of the support part is offset by 0.2 mm toward the origin point of the X axis and a shape such that the outer circumference side edge part is offset by 1.0 mm toward the origin point; and with the orthogonal coordinate system, a tip part of the support part is positioned in a region where the Y coordinate value is greater than a radius value of the optical part and outside a circumference of 5.0 mm in radius having the origin point as a center.

The inventors more focused on the outer circumference region of a posterior capsule which is remote further to the outer circumference side than the center part of the posterior capsule for which secondary cataracts are a problem. Specifically, a secondary cataract is due to propagation of crystalline lens epithelial cells at the overlapping surface of the optical part on the center part of the posterior capsule, and the inventors of the present invention focused on propagation of crystalline lens epithelial cells at the outer circumference region of the posterior capsule which houses the support part and is remote from the optical part to the outer circumference side.

Specifically, it is believed that the crystalline lens epithelial cells have a tendency to easily remain in the outer circumference region of the posterior capsule when doing surgery to implant an intraocular lens, and the remaining crystalline lens epithelial cells gradually propagate from the outer circumference region of the posterior capsule toward the inner circumference side, so that in many cases they spread onto the surface of the optical part from the outer circumference edge part of the optical part. Based on this viewpoint, the inventors of the present invention believed that if they could inhibit propagation of crystalline lens epithelial cells in the outer circumference region of the posterior capsule, they would not expand as far as the optical part, and it would be possible to prevent the onset of a secondary cataract. Also, as a result of extensive research and study, the inventors of the present invention discovered that at the outer circumference region of the posterior capsule, after removal of the crystalline lens, the overlapping of the anterior capsule and the posterior capsule directly to each other in a tightly adhered state is effective in suppressing propagation of crystalline lens epithelial cells.

However, with the single-piece intraocular lens of the conventional structure, as described previously, due to making the support part width dimension and thickness dimension larger, or to using an elbow design with a narrow width part hollowed in a small diameter arc state for the base end part or swelling in a convex shape at the inner circumference side edge part of the support part with the objective of increasing the strength of the support part and the like, they found that it is difficult to tightly adhere the anterior capsule and the posterior capsule at the outer periphery of the support part. Therefore, at the periphery of the support part, a region where the anterior capsule and the posterior capsule face each other with a distance open due to not being tightly adhered becomes large, and in this region that is not tightly adhered, it is thought that secondary cataracts occur easily due to the creation of an environment where crystalline lens epithelial cells propagate easily.

Here, with the intraocular lens with a structure according to the present invention, first, in regards to the outer circumference side edge part of the support part, that base part has a curved concave shape such that the center of curvature is set remote to the outer circumference side. By so doing, in the vicinity of the outer circumference side edge part of the support part, especially with the base part for which a gap is likely to occur between facing surfaces of the anterior capsule and the posterior capsule, the anterior capsule and the posterior capsule are tightly adhered up to a position proximal to the support part, making it possible to inhibit propagation of crystalline lens epithelial cells. Specifically, if a convex shape is imparted to the base part of the outer circumference side edge part of the support part and directly connecting that part to the outer circumference edge part of the optical part, an angular corner is generated at the connection part of the optical part and the support part, making it difficult to tightly adhere the anterior capsule and the poster capsule. On the other hand, in accordance with the present invention, by having the base part of the outer circumference side edge part of the support part be a curved concave shape, it is possible to avoid the occurrence of that kind of angular corner. In fact, by making the outer circumference side edge part at the base part of the support part be a curved concave shape, by setting the gap distance between the outer circumference side edge part of the support part and the lens capsule equator to be large, it is possible to make it even easier to tightly adhere the anterior capsule and the posterior capsule further to the outer circumference side than the support part.

Also, with the intraocular lens using the structure according to the present invention, by using 5.25 to 7.50 mm as the radius of curvature of the outer circumference side edge part of the support part that has a curved convex shape and extends toward the tip side, the position within the capsule and the shape of the support part in the implanted state are stabilized, and it is possible to obtain a better tightly adhered state between the anterior capsule and the posterior capsule. Specifically, by the support part receiving abutting reaction force by the equator part within the capsule in an implanted state, combined with post-operative capsule contraction, deformation displacement is made to occur in the direction with the support part approaching the optical part. At that time, by making the radius of curvature of the outer circumference side edge part of the support part be 5.25 mm or greater, it is possible to prevent obstacles to tight adherence of the anterior and posterior capsules between the tip part of the support part and the optical part due to the tip part of the support part and the optical part getting excessively close. Also, by making the radius of curvature of the outer circumference side edge part of the support part be 7.50 mm or less, it is possible to prevent the substantial thickening and the occurrence of local angular parts of the support part due to buckling at the middle part in the lengthwise direction of the support part, and furthermore to prevent obstacles to tight adherence of the anterior and posterior capsules near the support part due to the occurrence of capsular wrinkles (striations) that occur along with that.

Furthermore, with the intraocular lens using the structure according to the present invention, in regards to the inner circumference side edge part of the support part, in a region where the Y coordinate value is 1.0 mm or greater, the inner circumference side edge part of the support part is positioned between a shape such that the X coordinate value of the outer circumference side edge part of the support part is offset by 0.2 mm toward the geometric center of the optical part and a shape such that it is offset by 1.0 mm. In this way, by using a shape such that the inner circumference side edge part of the support part roughly follows the outer circumference side edge part, it is possible to have the distortion of the anterior and posterior capsules sandwiching the support part be roughly fixed in the circumference direction, and possible to effectively avoid obstructions to tight adherence of the anterior and posterior capsules due to stress and distortion concentration or the occurrence of capsular wrinkles or the like caused by a difference in distortion in the circumference direction. When the offset volume exceeds 1.0 mm, the width dimension of the support part becomes large, and the support part and the optical part are too close in the implanted state, so that tight adherence of the anterior and posterior capsules becomes difficult. Also, when the offset volume is less than 0.2 mm, it becomes difficult to stabilize the width dimension and strength of the support part, and there is also the risk of obstruction to tight adherence of the anterior and posterior capsules due to buckling or the like of the support part. With this mode, more preferably, in the region where the Y coordinate value is 1.0 mm or greater, the inner circumference side edge part of the support part is positioned between a shape such that the outer circumference side edge part of the support part is offset by 0.3 mm toward the geometric center of the optical part and a shape such that the offset is 0.9 mm.

In addition, with the intraocular lens having the structure according to the present invention, by positioning the support part tip part to outside the circumference of 5.0 mm in radius, as described above, with the support part formed having a width dimension of 0.2 to 1.0 mm, it is possible to effectively prevent excessive approaching toward the optical part due to the abutting reaction force on the equator part within the capsule that is applied in the implanted state. Specifically, while the optimal width dimension and inner and outer circumference edge part shapes are set for the support part, even between the tip part of the support part and the optical part which easily come close to each other due to capsule contraction or the like, it is possible to ensure an effective gap distance, and to have stable tight adherence of the anterior and posterior capsules.

The second mode of the present invention provides the intraocular lens according to the first mode, wherein a thickness dimension of the support part is 0.15 mm to 0.60 mm.

With the intraocular lens with a structure according to this mode, by having the thickness dimension of the support part be 0.15 mm or greater, strength of the support part is ensured, and buckling or the like in the implanted state is prevented, so that it is possible to have an even more stable tightly adhered state of the anterior and posterior capsules at the support part and its periphery. Also, by having the thickness dimension of the support part be 0.60 mm or less, it is possible to have the anterior and posterior capsules be tightly adhered up to a position even more close to the inner and outer circumference edges of the support part. With this mode, the thickness dimension of the support part is more preferably set within a range of 0.25 to 0.55 mm. Also, the material of the support part including the optical part preferably uses a soft type acrylic material, and by so doing, while satisfying the thickness dimensions according to this mode, it is possible to achieve at a high level the positioning of the optical part by the support part, the strength required for buckling resistance, and easy bending deformation characteristics when doing intraocular insertion and the like.

The third mode of the present invention provides the intraocular lens according to the first or second mode, wherein the inner circumference side edge part of the support part positioned in a region where the Y coordinate value is 1.0 mm or greater has a curved concave shape extending across a length of 70% or greater thereof from a base side of the support part toward the tip side.

With the intraocular lens with the structure according to this mode, by the inner circumference side edge part of the support part having a curved concave shape whose the center of curvature is positioned at the optical part side and extending across a wide range of 70% or greater thereof, an even larger gap distance is ensured between the inner circumference side edge part of the support part and the outer circumference edge part of the optical part. Thus, it is possible to even further improve the tight adherence of the anterior and posterior capsules in the region between the support part and the optical part. In this connection, at the tip side of the support part, in cases such as when providing a wide site for suture fixation or the like, there are cases when the inner circumference side edge part has a curved convex shape. However, even in cases when providing such a wide site, by having the inner circumference side edge part of the support part be a curved concave shape that extends across a length of 70% or greater thereof from the base side toward the tip side, it is possible to realize this mode. Also, with this mode, the inner circumference side edge part of the support part that has a curved concave shape does not need to have a fixed radius of curvature across its entirety, and for example, it is also possible to constitute a curved concave shape with smooth connection of a plurality of types of curved parts, or having a gradually changing curvature.

The outer circumference side edge part of the support part, in a region where the Y axis coordinate value is 1.0 mm or greater, preferably has a curved convex shape whose center of curvature is positioned to the optical part side and extending across 70% or greater, more preferably 80% or greater, and even more preferably substantially the entire length thereof. By so doing, for example, it is possible to prevent a region where the curved concave shape of the base part of the support part becomes excessively long or the like. Besides, in particular with the third mode noted above, the outer circumference side edge part and the inner circumference side edge part of the support part can have a similar shape or a roughly analogous shape, and by avoiding local stress or concentration of distortion at the anterior and posterior capsules positioned on the support part and its periphery, it is possible to have more stable tight adherence of the anterior and posterior capsules.

The fourth mode of the present invention provides the intraocular lens according to the third mode, wherein the inner circumference side edge part of the support part has a curved concave shape extending entirely from the base part of the support part to a position where the Y axis coordinate value is 1.0 mm.

With the intraocular lens with the structure according to this mode, it is possible to further improve the tight adherence of the anterior and posterior capsules between the inner circumference side edge part of the support part and the outer circumference edge part of the optical part, and possible to more effectively prevent propagation of crystalline lens epithelial cells in the outer circumference region adjacent to the optical part.

The fifth mode of the present invention provides the intraocular lens according to any of the first to fourth modes, wherein the inner circumference side edge part of the support part has a curved concave shape with a roughly fixed radius of curvature set within a range of 0.3 to 0.7 mm at the base part of the support part extending across both sides sandwiching a contact point with the X axis.

With the intraocular lens having the structure according to this mode, the radius of curvature of the inner circumference side edge part at the base part of the support part is 0.3 mm or greater. Thus, it is possible to prevent the existence of corner parts caused by the radius of curvature of the curved concave shape being too small, which make tight adherence of the anterior and posterior capsules difficult. Also, by having that radius of curvature be 0.7 mm or less, it is possible to prevent obstacles to tight adherence of the anterior and posterior capsules that come with an increase in the risk of the occurrence of buckling of the support part or capsular wrinkles (striations) caused by the abutting reaction force to the equator part inside the capsule at the tip of the support part becoming too big.

With this mode, preferably, combination with the third or fourth mode is employed, and as a result, the inner circumference side edge part of the support part has a curved concave shape in a broad region starting from the base part of the support part toward the tip side, more preferably at the region extending across substantially the entire length. Also, with this mode, preferably, the base part of the inner circumference side edge part of the support part is constituted having substantially an arc shape such that the radius of curvature is roughly fixed within a range of 0.3 to 0.7 mm. By so doing, the base part of the inner circumference side edge part of the support part has an even smoother shape. Thus, by more effectively avoiding concentration of distortion or stress, it is possible to further improve the tight adherence of the anterior and posterior capsules.

The sixth mode of the present invention provides the intraocular lens according to any of the first to fifth modes, wherein a width dimension in an X axis direction of the support part at a position where the Y coordinate value is the radius value of the optical part is larger than a width dimension in the X axis direction of the support part at a position where the Y coordinate value is 1.0 mm.

With the intraocular lens having the structure according to this mode, it is possible to avoid the situation where the distance between the outer circumference edge part of the optical part and the inner circumference edge part of the support part in the implanted state excessively changes in the support part lengthwise direction. Specifically, in a state with the intraocular lens implanted, even when considering the support part having deformation displacement to the optical part side in accordance with capsule contraction or the like, the distance between the support part and the optical part can easily become larger rapidly starting from the base part of the support part toward the tip side. In light of that, with this mode, by setting the width dimension from the base side of the support part toward the tip side to become larger smoothly, by inhibiting a rapid increase in the distance between the support part and the optical part in the circumference direction of the optical part, and forming a region that is smoothly connected in the circumference direction of the optical part, it is possible to further improve tight adherence of the anterior and posterior capsules.

The seventh mode of the present invention provides the intraocular lens according to any of the first to sixth modes, wherein the support part is positioned within a circumference of 7.5 mm in radius having the origin point of the orthogonal coordinate system as the center.

With the intraocular lens having the structure according to this mode, it is possible to effectively avoid problems such as, for example, the abutting reaction force of the tip part of the support part toward the equator part inside the capsule in an implanted state becoming excessively large and inducing an increase in the risk of buckling of the support part or the occurrence of capsular wrinkles (striations).

Effect of the Invention

The present invention realizes an intraocular lens of a novel structure that newly focuses on the outer circumference region of the posterior capsule which is remote to the outer circumference side from the center part of the posterior capsule for which secondary cataracts are a problem, and that is able to inhibit the propagation of crystalline lens epithelial cells in the outer circumference region of that posterior capsule. In particular, the present invention is able to provide an intraocular lens of a novel structure that can realize tight adherence of the anterior and posterior capsules based on the finding that, in the outer circumference region of the posterior capsule, focusing on the propagation mechanism of the crystalline lens epithelial cells that occurs due to the existence of the support part, the tight adherence of the anterior and posterior capsules is effective in the inhibition of that propagation of crystalline lens epithelial cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

EMBODIMENTS FOR CARRYING OUT THE INVENTION

Figure 1:
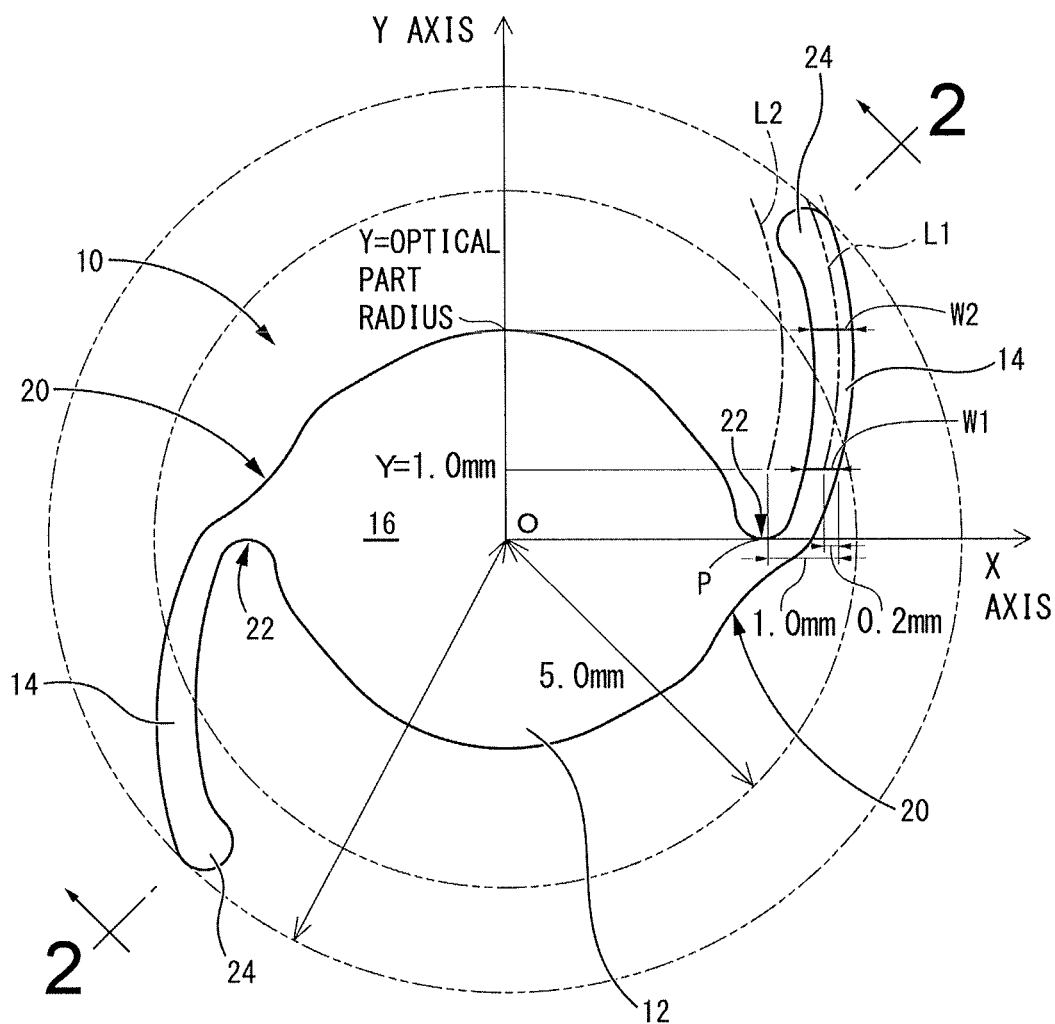
FIG. 1 is a front view of an intraocular lens as a first embodiment of the present invention.

Following, we will describe an embodiment of the present invention while referring to the drawings.

Figure 2:
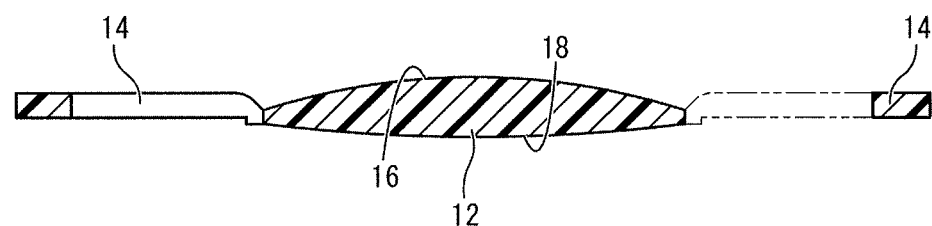
FIG. 2 is a cross section view taken along line 2-2 of FIG. 1.

First, in FIGS. 1 and 2, a foldable type intraocular lens 10 is shown as a first embodiment of the present invention. With this intraocular lens 10, an optical part 12 and a pair of support parts 14, 14 are integrally formed.

In more specific detail, the optical part 12 has a disc shape such that the front view exhibits roughly a circular shape. With this optical part 12, a lens region is constituted equipped with optical characteristics that fulfill a substitution function of the crystalline lens of the human eye. Also, the optical part 12 has optical characteristics according to each shape of a front surface (cornea side surface) 16 and rear surface (retina side surface) 18, and with this embodiment, by imparting a spherical convex surface to both the optical part front surface 16 and the optical part rear surface 18, the optical part 12 has a convex lens shape.

Also, the support parts 14, 14 extend toward the outer circumference side from two locations positioned facing each other in the radial direction of the outer circumference edge part with the optical part 12, and extend inclining in the circumferentially reverse direction. Also, each support part 14, 14 is curved and extends out, and the tip parts are free ends. Also, the support parts 14, 14 of this embodiment have the same shape, and are mutually point symmetrical in relation to the geometric center O of the optical part 12.

However, with the intraocular lens 10 having the optical part 12 and the support parts 14, 14 in this way, in addition to being equipped with sufficient visible light ray transmittance to give a foldable type intraocular lens, the lens is formed using various types of soft material having excellent flexibility and a certain level of elasticity. Preferably, a soft material for which the 100% distortion secant modulus of elasticity is 0.1 to 5.0 MPa is used. This is because if the 100% distortion secant modulus of elasticity is smaller than 0.1 MPa, the intraocular lens is too soft, and during intracapsular insertion, there is the risk of not having the shape of the intraocular lens maintained sufficiently. On the other hand, when the 100% distortion secant modulus of elasticity is greater than 5.0 MPa, the intraocular lens is too hard, and there is the risk of folding of the intraocular lens during intra-capsular insertion being difficult. Also, preferably, the lens is formed using a soft material for which the glass transition temperature is 30° C. or less, and the index of refraction is 1.51 or greater.

By using this kind of soft material, bending deformation is possible with which the intraocular lens 10 is easily folded and wound up under normal temperatures. Thus, it is possible to have the intraocular lens 10 be even more compact, so as to even more easily perform insertion into the capsule during implanting.

In particular, the thickness dimension of the support parts 14 (the vertical direction dimension in FIG. 2) is preferably 0.15 mm to 0.60 mm, more preferably 0.25 mm to 0.55 mm, and with this embodiment, is set to 0.35 mm. By having the thickness dimension of the support parts 14 be in the range noted above, it is possible to ensure sufficient strength of the support parts 14, and possible to even more easily obtain bending deformation.

Here, as the specific forming material for the intraocular lens 10, it is possible to use any known soft material used for intraocular lenses from the past, but among those, to obtain an intraocular lens with excellent shape recoverability, as shown below in (i) it is preferable to use monomers containing one or two or more (meth)acrylic acid esters. Also, as shown below in (ii), any monomer can be mixed as appropriate. Furthermore, as necessary, as shown below in (iii), additives can be added as necessary.

(i) Included Monomers

Linear, branched, or cyclic alkyl (meth)acrylates such as the following:

methyl (meth)acrylate, ethyl (meth)acrylate, butyl (meth)acrylate, cyclohexyl (meth)acrylate or the like.

Hydroxyl group-containing (meth)acrylates such as the following:

hydroxy ethyl (meth)acrylate, hydroxyl butyl (meth)acrylate, diethylene glycol mono (meth)acrylate or the like.

Aromatic ring-containing (meth)acrylates such as the following:

phenoxy ethyl (meth)acrylate, phenyl (meth)acrylate, phenyl ethyl (meth)acrylate or the like.

Silicon-containing (meth)acrylates such as the following:

trimethyl siloxy dimethyl silyl methyl (meth)acrylate, trimethyl siloxy dimethyl silyl propyl (meth)acrylate or the like.

Note that "(meth)acrylate" is a general name for two compounds including " . . . acrylate" as well as " . . . methacrylate," and the same is true for other (meth)acrylic derivatives described hereafter.

(ii) Optional Monomers (Meth)acrylamide and its derivatives such as the following:

(meth)acrylamide, N,N-dimethyl (meth)acrylamide or the like.

N-vinyl lactams such as the following:
N-vinyl pyrrolidone or the like.
Styrene or its derivatives.
Cross linking monomers such as the following:
butanediol di(meth)acrylate, ethylene glycol di(meth)acrylate.

(iii) Additives

Thermal polymerization initiators, photo polymerization initiators, photosensitizers or the like.

Dyes or the like.

Ultraviolet absorbers or the like.

Also, using this kind of monomer material, when integrally forming the intraocular lens 10, it is possible to use any of various methods known from the past, and it is possible to obtain the target intraocular lens 10 using a cutting and machining molding method or a mold molding method, for example. Using the cutting and machining molding method, after forming a lens blank of a suitable shape such as a rod shape, block shape, plate shape or the like by polymerizing designated polymerization components comprising monomer materials as described above, it is possible to obtain the intraocular lens 10 of the desired shape by using a lathe or the like to implement cutting and machining on the lens blank. Also, using the mold molding method, using a molding mold having a molding cavity corresponding to the shape of the target intraocular lens 10, a designated polymerization component comprising a monomer material as described above is introduced inside the molding cavity, and by implementing a suitable polymerization operation there, it is possible to obtain the intraocular lens 10 of the desired shape. In particular, with this embodiment, since the optical part 12 and the support parts 14, 14 are integrally formed, it is possible to even more easily form the intraocular lens 10. As the polymerization method for the monomer material, it is possible to use as appropriate thermal polymerization methods, photo polymerization methods known from the past, or a polymerization method that combines these or the like.

This kind of intraocular lens 10 is inserted in a folded shape inside the lens capsule after the crystalline lens has been removed when treating a cataract or the like. Then, after insertion of the intraocular lens 10, the shape of the intraocular lens 10 returns, and while the tip parts of the support parts 14, 14 are abutting the circumference edge part of the lens capsule, the optical part 12 is held in a designated position at the center inside the lens capsule.

Here, at the outer circumference side edge part of the support parts 14, 14 with the intraocular lens 10, an outer circumference base end part 20 which is the base part of the support part 14 has a curved concave shape which is concave with respect to the outer circumference side. Also, the outer circumference side edge part of the support part 14 that ranges from the circumferential end part of this outer circumference base end part 20 to the tip part of the support part 14 has a curved convex shape that is convex with respect to the outer circumference side, and the outer circumference side edge part of the support part 14 is constituted so that there is smooth connection of the curved concave shape part and the curved convex shape part. The radius of curvature of the part having a curved convex shape at the outer circumference side edge part of the support part 14 is 5.25 mm to 7.50 mm, and with this embodiment, is roughly 6.0 mm. This is because since the diameter of the lens capsule that has typically shrunk after surgery is around 10.5 mm, if the radius of curvature of the curved convex shape of the outer circumference of the support part 14 is 5.25 mm or less, there is the risk that the tip part of the support part 14 will become wound during contraction of the lens capsule, and that there will be obstruction of tight adherence of anterior and posterior capsules 28 and 30 described later. On the other hand, if the radius of curvature is 7.5 mm or greater, there is the risk that buckling of the support part 14 or capsular wrinkles will occur during contraction of the lens capsule, and that there will be obstruction of tight adherence of the anterior and posterior capsules 28 and 30.

Here, as shown in FIG. 1, using the geometric center O of the optical part 12 as the origin point, we will assume an orthogonal coordinate system for which the direction of the straight line that passes through the origin point and touches an inner circumference base end part 22 which is the base part of the inner circumference side of the support part 14 is the X axis direction (the lateral direction in FIG. 1), and the direction that is orthogonal to the X axis is used as the Y axis direction (vertical direction in FIG. 1). With this embodiment, the inner circumference base end part 22 has a curved concave shape, and the straight line that connects the vertex P of this inner circumference base end part 22 and the origin point O is the X axis direction. Since the intraocular lens 10 of this embodiment has point symmetry with respect to the geometric center O of the optical part 12, we will describe this using the right half of FIG. 1.

Furthermore, with this embodiment, with the orthogonal coordinate system noted above, the inner circumference side edge part of the support part 14 has a curved concave shape extending entirely from the vertex P of the inner circumference base end part 22 where the X coordinate value is smallest to the position where the Y axis coordinate value is 1.0 mm.

The inner circumference base end part 22 that has a curved concave shape preferably has a roughly fixed radius of curvature set within a range of 0.3 to 0.7 mm at both sides sandwiching the vertex P, and with this embodiment, at both sides sandwiching the vertex P, this is an arc shape close to a semicircle having a radius of curvature of roughly 0.5 mm. This is because if the radius of curvature at the inner circumference base end part 22 is smaller than 0.3 mm, the support parts 14 get too close to the optical part 12, so the abutting surface area between the outer circumference edge part of the support parts 14 and the circumference edge part of the lens capsule decreases, and there is the risk of the holding effect of the optical part 12 by the support parts 14 not being sufficiently exhibited. On the other hand, if the radius of curvature is greater than 0.7 mm, there is the risk that the support part 14 and the circumference edge part of the lens capsule will strongly abut, with the risk of buckling of the support part 14 or capsular wrinkles occurring, and therefore, there is the risk of an obstruction to the tight adherence of the anterior and posterior capsules 28 and 30 at the lens capsule described later.

Also, in the region where the Y coordinate value is 1.0 mm or greater with the orthogonal coordinate system noted above, when the curved line such that the outer circumference side edge part of the support parts 14 is offset by 0.2 mm toward the X axis origin point, specifically, toward the geometric center of the optical part 12 is L1, and the curved line such that the outer circumference side edge part is offset by 1.0 mm toward the origin point is L2, the inner circumference side edge part of the support parts 14 is positioned between L1 and L2. Also, with this embodiment, the curved concave shape part is formed on the inner circumference side edge part of this support parts 14, and the curved concave shape part including the inner circumference base end part 22 in the region where the Y coordinate value is 1.0 mm or less and the curved concave shape part extending toward the tip in the region where it is 1.0 mm or greater are connected smoothly. As a result, at the inner circumference side edge part of the support parts 14, the part that is the curved concave shape can be ensured for a long region from the base end part to near the tip.

In this way, by having the L1 offset volume be 0.2 mm, the width dimension of the support parts 14 (lateral direction in FIG. 1) is 0.2 mm or greater, and it is possible to ensure sufficient strength of the support parts 14 with the intraocular lens 10 formed using a soft material. Furthermore, by having the L2 offset volume be 1.00 mm, the width dimension of the support parts 14 is 1.0 mm or less, it is possible to ensure sufficient space between the optical part 12 and the support parts 14, and it is possible to have stable tight adherence between the anterior and posterior capsules 28 and 30 of the lens capsule described later. Even more preferably, the L1 offset volume is 0.3 mm, and the L2 offset volume is 0.9 mm.

Furthermore, with this embodiment, a swelling part 24 is formed at the tip part of each support part 14, 14, and using the outer circumference edge of this swelling part 24, the outer circumference side edge part and the inner circumference side edge part of the support part 14 are connected smoothly. With the orthogonal coordinate system noted above, this swelling part 24 is positioned in a region where the Y coordinate value is greater than the radius value of the optical part 12, and outside a circumference of 5.0 mm in radius having the geometric center O of the optical part 12 as the center. Then, with this swelling part 24, the outer circumference side edge part and the inner circumference side edge part of the support parts 14 are connected in roughly a semicircular arc shape, and that swelling part 24 is shaped swelling further to the inner circumference side than the center part of the support part 14. Specifically, with the inner circumference side edge part of the support parts 14, with the tip part of the support parts 14, there is a curved convex shape that is convex in relation to the inner circumference side, and the curved concave shape part between the inner circumference base end part 22 and the swelling part 24 and the curved convex shape part with the swelling part 24 are connected smoothly. By the swelling part 24 being formed with the width dimension (lateral direction dimension in FIG. 1) becoming larger at the tip of the support parts 14 in this way, when the intraocular lens 10 is inserted into the capsule, it is possible to ensure a part abutting the circumference edge part of the lens capsule with stability for the support parts 14. Also, by positioning the swelling part 24 at outside a circumference of 5.0 mm in radius having the geometric center O of the optical part 12 as the center, even with a swelling part 24 with a large width dimension, a sufficient gap distance with the outer circumference edge part of the optical part 12 is ensured.

In this way, in the region where the Y coordinate value is 1.0 mm or greater with the orthogonal coordinate system noted above, it is not necessary that the inner circumference side edge part of the support parts 14 be a curved concave shape across the entire length thereof, and it is also possible that the curved convex shape part is formed like the swelling part 24, for example. The inner circumference side edge part of the support parts 14 in this region preferably has a curved concave shape extending across 70% or greater of the entire length from the base end side toward the tip side of the support parts 14. As a result, a sufficient space is ensured between the outer circumference edge part of the optical part 12 that is a circle and the inner circumference side edge part of the support parts 14 that is a curved concave shape, and it is possible to have stable tight adherence of the anterior and posterior capsules 28 and 30 of the lens capsule described later.

Furthermore, with this embodiment, compared to a width dimension W1 (see FIG. 1) in the X axis direction of the support parts 14 at a position where the Y coordinate value is 1.0 mm, a width dimension W2 (see FIG. 1) in the X axis direction of the support parts 14 at a position where the Y coordinate value is the radius of the optical part 12 is larger. As a result, when the support part 14 is bent during implanting of the intraocular lens 10, having the space between the inner circumference side edge part of the support parts 14 and the outer circumference edge part of the optical part 12 become too narrow is avoided, and it is possible to have stable tight adherence of the anterior and posterior capsules 28 and 30 of the lens capsule described later. In particular, with this embodiment, the width dimension becomes gradually larger as it goes from the base part of the support part 14 toward the tip part.

Also, as described above, the support parts 14 of this embodiment are positioned within a circumference of 6.5 mm in radius having the origin point O as the center with the orthogonal coordinate system noted above. Said another way, the outer circumference edge part of the swelling part 24 that is the tip of the support parts 14 abuts the circumference of 6.5 mm in radius. By having the support parts 14 positioned within the range noted above, it is possible to reduce the risk of adherence of the anterior and posterior capsules 28 and 30 being obstructed with the lens capsule by the occurrence of buckling of the support parts 14 or capsule wrinkles.

Figure 3:
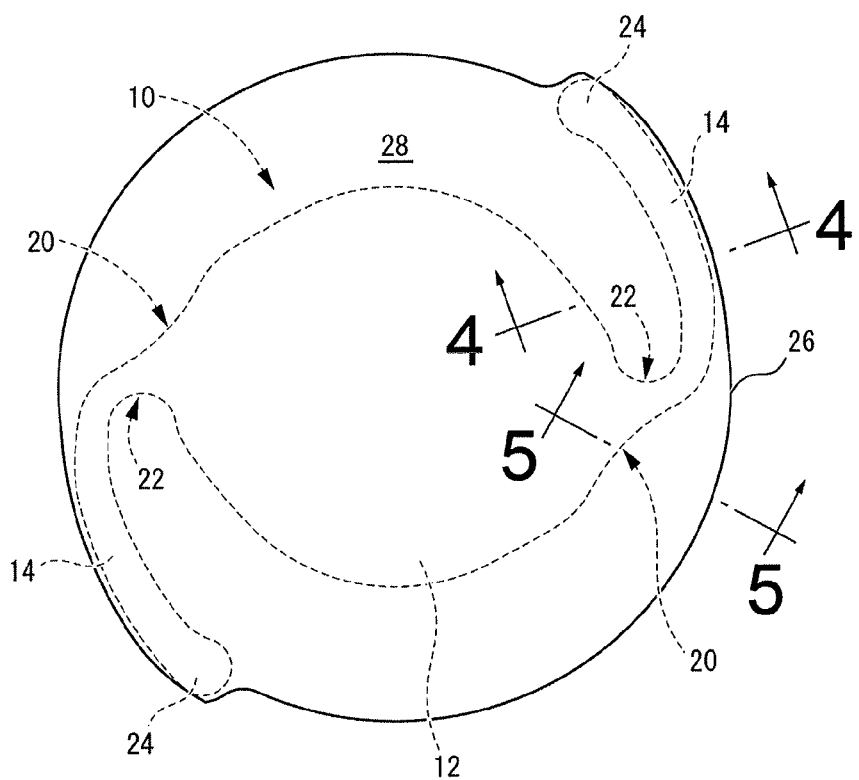
FIG. 3 is a front view showing the state of the intraocular lens shown in FIG. 1 implanted in the lens capsule.
Figure 4:
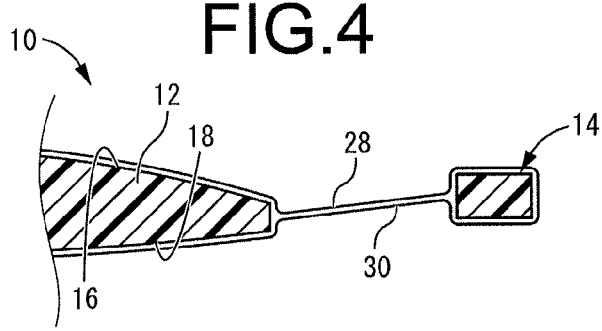
FIG. 4 is a cross section view taken along line 4-4 of FIG. 3.
Figure 5:
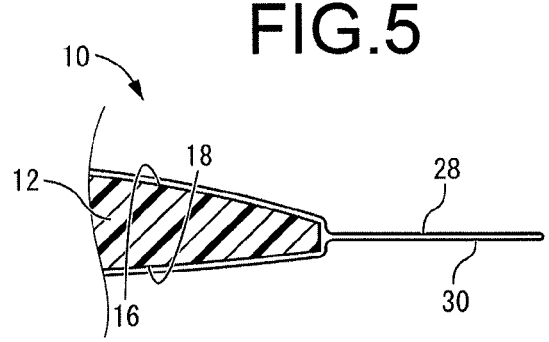
FIG. 5 is a cross section view taken along line 5-5 of FIG. 3.

Next, FIG. 3 to FIG. 5 schematically show the state of the intraocular lens 10 with a shape as described above in the implanted state, and show the state where the lens capsule has shrunk after surgery. In that state, as shown in FIG. 3, both support parts 14, 14 of the intraocular lens 10 abut an equator part 26 of the lens capsule for which the circumference of the lens capsule is the longest with a plan view, and the optical part 12 is held in a designated position within the lens capsule. Also, while the anterior capsule 28 which is the front side (cornea side) of the lens capsule is tightly adhered to the front side of the intraocular lens 10, the posterior capsule 30 which is the back side (retina side) of the lens capsule is tightly adhered to the back side of the intraocular lens 10. To remove the crystalline lens and insert the intraocular lens, a known cutting window having a smaller opening than the outer diameter of the optical part 12 provided at the center part of the anterior capsule 28 is omitted from the drawing to avoid being confused with the structure lines of the intraocular lens 10.

In more specific detail, by the lens capsule shrinking, the outer circumference side edge parts of the support parts 14 abut the equator part 26 inside the lens capsule, and each support part 14, 14 of the intraocular lens 10 implanted inside the lens capsule is pressed inward. The intraocular lens 10 is fixed on the inside of the lens capsule by the abutting reaction force of the support parts 14, 14, specifically, the optical part 12 of the intraocular lens 10 is held at a designated position inside the lens capsule. It is preferable that the outer circumference side edge part of the support parts 14 be tightly adhered across a length of half or more thereof in relation to the equator part 26 inside the lens capsule, but it is acceptable to have a slight gap therebetween.

Also, with the intraocular lens 10 inserted in the lens capsule in this way, the anterior capsule 28 is overlapped in a tightly adhered state on the front surfaces of the optical part 12 and each support part 14, and the posterior capsule 30 is overlapped in a tightly adhered state on the rear surfaces of the optical part 12 and each support part 14.

Here, with the intraocular lens 10, since the inner circumference side edge part of the support parts 14 is a curved concave shape, compared to an elbow design or the like for which a convex shaped part is provided like the conventional structure, it is possible to set the gap distance in the radial direction in relation to the optical part to be larger, and a space is effectively formed between the inner circumference side edge part of the support part 14 and the outer circumference edge part of the optical part 12. By making the span of the space that exists between the support part 14 and the optical part 12 larger in this way, it is possible to avoid the occurrence of a state where the anterior and posterior capsules 28 and 30 between both ends of the space project and stretch so as to not overlap with each other within the space, and it is possible to have the anterior capsule 28 and the posterior capsule 30 be deformed so as to wind around the outer circumference surface of the optical part 12 or the inner circumference surface of the support parts 14 and be tightly adhered to each other. As a result, as shown in FIG. 4, in the region between the outer circumference edge part of the optical part 12 and the inner circumference side edge part of the support parts 14, it is possible to have the anterior capsule 28 and the posterior capsule 30 be tightly adhered to each other, and since the propagation of crystalline lens epithelial cells in that region is inhibited, it is possible to exhibit an excellent inhibitory effect on the onset of secondary cataracts.

In particular, by the inner circumference side edge part of the support parts 14 being positioned between curved lines L1 and L2 which are the same shape as the outer circumference side edge part of the support parts 14, having a big difference between the shapes of the outer circumference side edge part and the inner circumference side edge part of the support part 14 is avoided, and it is possible to have stable tight adherence between the anterior and posterior capsules 28 and 30 of the lens capsule.

Also, with this embodiment, at the inner circumference side edge part of the support parts 14, a part having a curved concave shape is formed for both regions of the Y coordinate value with the orthogonal coordinate system noted above being 1.0 mm or less and being 1.0 mm or greater, and the part that has a curved concave shape is formed extending across a sufficient length. By so doing, a space is stably formed between the optical part 12 and the support parts 14, and it is possible to even more reliably achieve tight adherence between the anterior and posterior capsules 28 and 30 of the lens capsule.

Also, with the intraocular lens 10, the outer circumference base end parts 20 of the support parts 14 have a curved concave shape. By so doing, in the region further to the outer circumference side than the outer circumference base end part 20 with the intraocular lens 10, sufficient space is formed between the outer circumference base end part 20 and the lens capsule equator part 26. Also, during shrinking of the lens capsule, it is possible to have the anterior capsule 28 and the posterior capsule 30 be deformed so as to wrap around the outer circumference surface of the intraocular lens 10 and be tightly adhered to each other. As a result, as shown in FIG. 5, in the region further to the outer circumference side than the outer circumference base end part 20 with the intraocular lens 10, it is possible for the anterior capsule 28 and the posterior capsule 30 to be tightly adhered to each other, and since propagation of crystalline lens epithelial cells is inhibited in that region, it is possible to effectively inhibit the onset of secondary cataracts.

EXAMPLE

Figure 6:
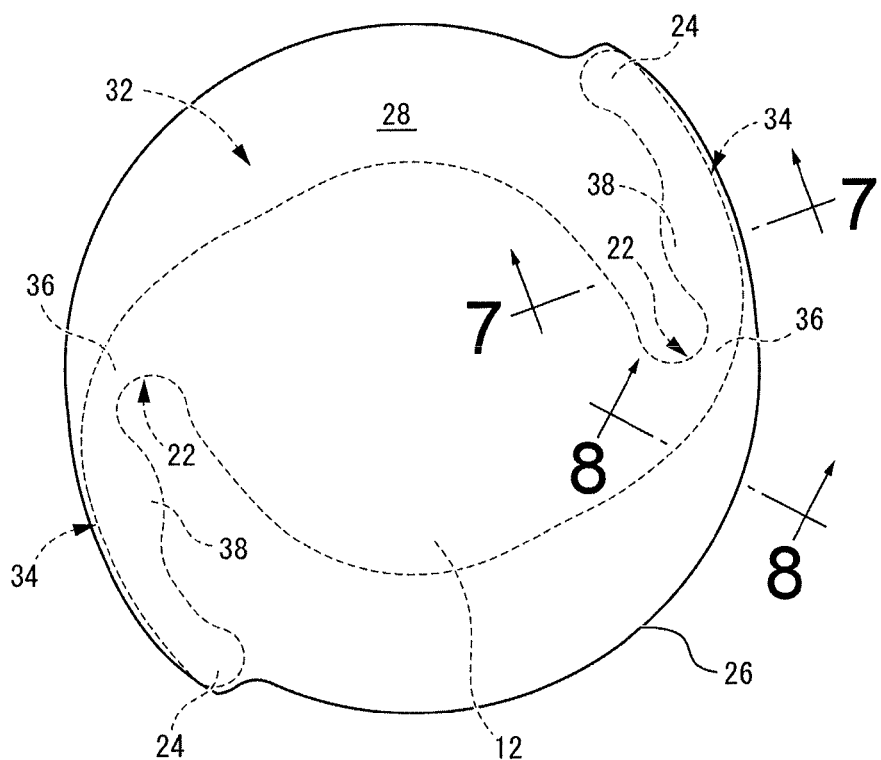
FIG. 6 is a front view showing the state of an intraocular lens as Comparative Example implanted in the lens capsule.

A trial product was made of the intraocular lens 10 according to the structure of the present invention, and comparison was done of the level of propagation of crystalline lens epithelial cells between the intraocular lens 10 of the present invention and the intraocular lens of the conventional structure. As the intraocular lens of the conventional structure, as shown in FIG. 6, an intraocular lens 32 having what is referred to as an elbow design was used. The intraocular lens 32 shown in FIG. 6 is implanted inside the lens capsule, and a state is shown with the lens capsule shrunk after surgery. Also, with the description hereafter, for parts that are substantially the same as those of the embodiment noted above, in the drawings, the same code number will be given as with embodiment noted above, and a detailed description will be omitted.

With this intraocular lens 32 of the conventional structure, in contrast to the intraocular lens 10 of the present invention, a curved concave shape part is not formed at the outer circumference side base end parts of support parts 34, and the outer circumference edge part of the support parts 34 and the outer circumference edge part of the optical part 12 are convex at the outer circumference side and are connected in a smooth curved line. Also, at the base end part of the support parts 34, a narrow hinge part 36 is formed to make it easy for the support parts 34 to bend, and a broad part 38 which is relatively wider at the tip side than the hinge part 36 is formed at the support parts 34 continuous with the hinge part 36. Specifically, a curved convex shape is formed at the middle part in the lengthwise direction on the inner circumference side edge part of the support parts 34.

Figure 7:
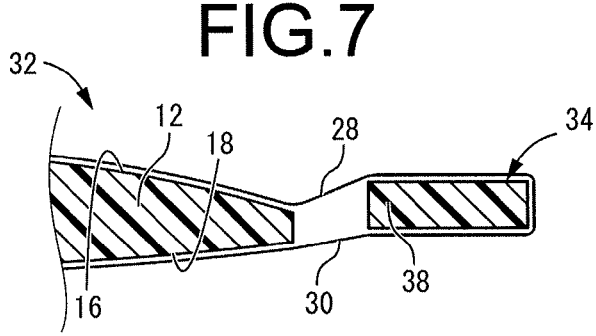
FIG. 7 is a cross section view taken along line 7-7 of FIG. 6.

With the intraocular lens 32 of the conventional structure with this kind of shape, the broad part 38 which has a curved convex shape is formed at the middle part in the lengthwise direction of the inner circumference side edge part of the support parts 34, so at the region between the outer circumference edge part of the optical part 12 and the inner circumference side edge part of the support parts 34, sufficient space is not formed. Therefore, as shown in FIG. 7, during shrinking of the lens capsule, it is not possible for the anterior capsule 28 and the posterior capsule 30 to wrap around the outer circumference surface of the optical part 12 or the inner circumference surface of the support parts 34, and at the region between the outer circumference edge part of the optical part 12 and the inner circumference side edge part of the support parts 34, the anterior capsule 28 and the posterior capsule 30 do not tightly adhere, and are remote by a designated distance, specifically, they face each other while having a gap.

Figure 8:
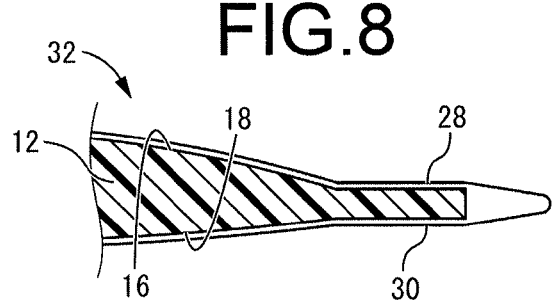
FIG. 8 is a cross section view taken along line 8-8 of FIG. 6.

Also, for the outer circumference side base end part of the support parts 34, a part that has a curved concave shape is not formed, so the remote distance between the outer circumference side base end part of the support parts 34 and the equator part of the lens capsule is made smaller. Therefore, as shown in FIG. 8, during shrinking of the lens capsule, the anterior capsule 28 and the posterior capsule 30 are not able to wrap around the outer circumference surface of the intraocular lens 32, and in the region further to the outer circumference side than the outer circumference side base end part of the support parts 34, the anterior capsule 28 and the posterior capsule 30 are not tightly adhered, and they have a gap of a designated size.

Here, a trial product was made of the intraocular lens 10 according to the structure of the present invention as the intraocular lens of Example. The intraocular lens 10 of Example has a full length (length from the outermost circumference end of one support part 14 to the outermost circumference end of the other support part) of 13.0 mm, an optical part 12 diameter of 5.5. mm, and a standard power of +20.0 D. On the other hand, for the intraocular lens 32 of Comparative Example, used was an Acrys of (registered trademark) (1P) model SA30AT made by Alcon, Inc. having the structure noted above. With the intraocular lens 32 of Comparative Example as well, the full length was 13.0 mm, the optical part 12 diameter was 5.5 mm, and the standard power was +20.0 D.

Then, the intraocular lens 10 according to the structure of the present invention as the intraocular lens of Example and the intraocular lens 32 using the structure noted above as the intraocular lens of Comparative Example were implanted into rabbit eyes, and the level of propagation of crystalline lens epithelial cells was observed. For the rabbits, Japanese white males were used, and these were purchased from Kitayama Labs Co., Ltd. Also, experiments were performed using three rabbits for the intraocular lens 10 of Example, and experiments were performed using three rabbits for the intraocular lens 32 of Comparative Example. The weight of the rabbits at the time of implanting was from 2.05 to 3.58 kg.

As the experimentation method, for three rabbits, the crystalline lens was removed and the intraocular lens 10 was implanted, and for three rabbits, the crystalline lens was removed and the intraocular lens 32 was implanted. After that, after raising them for three weeks, the eyeballs were removed from each rabbit, the lens capsules were observed using an optical microscope, and images were taken using a CCD camera.

Figure 9:
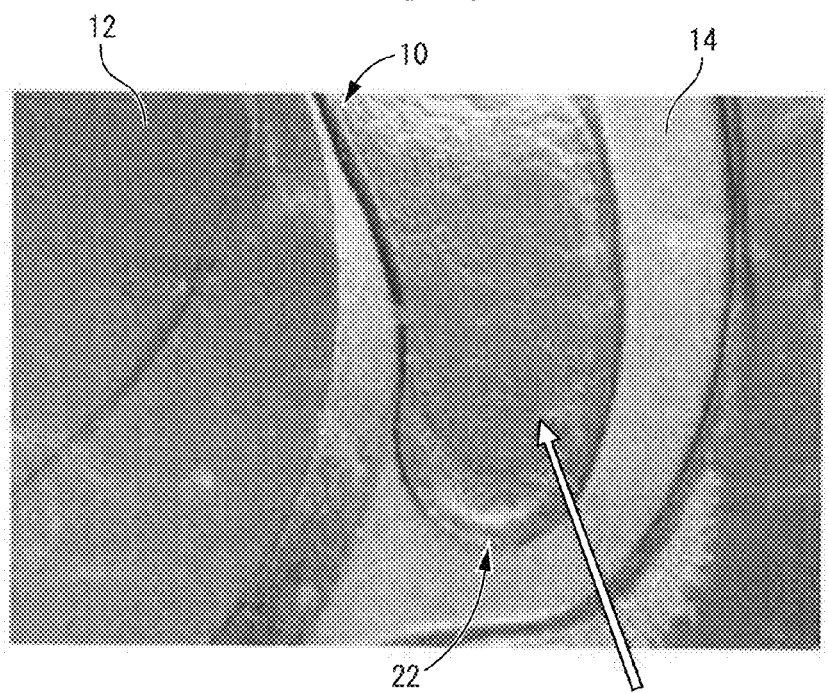
FIG. 9 is a photograph showing the result of the intraocular lens shown in FIG. 1 being implanted in a rabbit eye.
Figure 10:
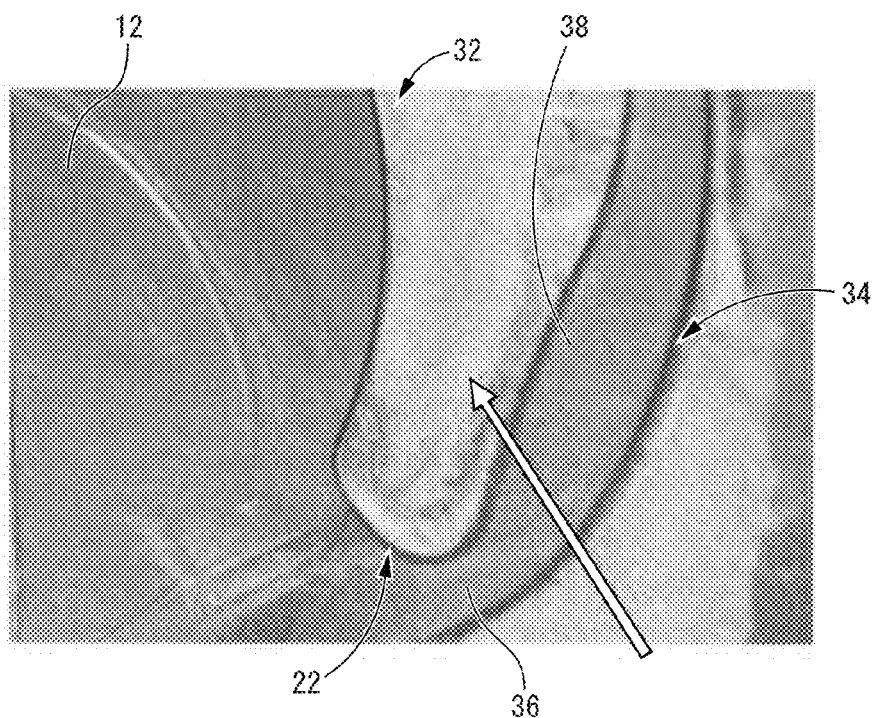
FIG. 10 is a photograph showing the result of the intraocular lens shown in FIG. 6 being implanted in a rabbit eye.

FIGS. 9 and 10 respectively show examples of the results of Example and Comparative Example. Here, when the regions between the outer circumference edge part of the optical part 12 and the inner circumference side edge part of the support parts 14 (34) were compared for the respective intraocular lenses (the regions shown with the white arrow in FIGS. 9 and 10), with the photograph of Comparative Example (FIG. 10), the aforementioned region was white and cloudy, and it was found that the crystalline lens epithelial cells remaining within the lens capsule when the crystalline lens was removed were propagating.

These results are due to the fact that in comparison to the intraocular lens 32 of the conventional structure having a gap in which the anterior capsule 28 and the posterior capsule 30 in the region noted above are not tightly adhered, the intraocular lens 10 according to the structure of the present invention does not have a gap, and the anterior capsule 28 and the posterior capsule 30 in the region noted above are tightly adhered. Specifically, with the intraocular lens 32 of the conventional structure, the crystalline lens epithelial cells propagate in the gap between the anterior and posterior capsules 28 and 30, and white cloudiness is seen in the aforementioned region. On the other hand, with the intraocular lens 10 according to the structure of the present invention, there is no gap between the anterior and posterior capsules 28 and 30 in the aforementioned region. This will limit propagation of the crystalline lens epithelial cells, whereby white cloudiness of the aforementioned region is not observed.

Therefore, when treating a cataract in the human eye, by using the intraocular lens 10 according to the structure of the present invention, propagation of the crystalline lens epithelial cells remaining in the lens capsule is effectively inhibited, and it is possible to reliably reduce the risk of the onset of a secondary cataract as well.

Above, we gave a detailed description of the embodiment and Example of the present invention, but the present invention is not limited to those specific descriptions. For example, in the preceding embodiment, the radius of curvature of the part that has a curved convex shape at the outer circumference side edge part of the support parts 14 is fixed at 6.0 mm. However, it is also possible to have a shape such that parts having a plurality of radii of curvature are smoothly connected, or alternatively to have a shape such that the radius of curvature gradually changes. With this mode, the respective radii of curvature are acceptable as long as they are in a range from 5.25 to 7.50 mm. With the inner circumference side edge part of the support parts 14 as well, the radius of curvature of the part that has a curved concave shape can be fixed, or it can also have a plurality of radii of curvature.

Also, in the preceding embodiment, the width dimension of the support parts 14 gradually becomes larger as the support parts 14 go from the base part to the tip part, but the invention is not limited to that embodiment. For example, it is also possible for the support parts 14 to have a fixed width dimension along the entire length. Specifically, the swelling part 24 at the tip of the support part 14 is not essential.

KEYS TO SYMBOLS

10: Intraocular lens, 12: Optical part, 14: Support part, 20: Outer circumference base end part, 22: Inner circumference base end part

The invention claimed is:

1. An intraocular lens comprising:
   an optical part formed of a bendably deformable soft material; and
   a support part integrally provided to the optical part, the support part extending from the optical part toward an outer circumference side while inclining in a circumference direction, wherein
   an outer circumference side edge part of the support part has a curved concave shape at a base part thereof, and has a curved convex shape with a radius of curvature of 5.25 to 7.50 mm at a portion further to a tip side thereof than the base part,
   an inner circumference side edge part of the support part has a curved concave shape at a base part thereof, and with an orthogonal coordinate system for which a geometric center of the optical part is an origin point, a tangent line to the base part of the inner circumference side edge part is an X axis, and an orthogonal line to the X axis is a Y axis, in a region where a Y coordinate value is 1.0 mm or greater, the inner circumference side edge part of the support part is positioned between a shape such that the outer circumference side edge part of the support part is offset by 0.2 mm toward the origin point of the X axis and a shape such that the outer circumference side edge part is offset by 1.0 mm toward the origin point, and
   with the orthogonal coordinate system, a tip part of the support part is positioned in a region where the Y coordinate value is greater than a radius value of the optical part and outside a circumference of 5.0 mm in radius having the origin point as a center.

2. The intraocular lens according to claim 1, wherein a thickness dimension of the support part is 0.15 mm to 0.60 mm.

3. The intraocular lens according to claim 1, wherein the inner circumference side edge part of the support part positioned in a region where the Y coordinate value is 1.0 mm or greater has a curved concave shape extending across a length of 70% or greater thereof from a base side of the support part toward the tip side.

4. The intraocular lens according to claim 3, wherein the inner circumference side edge part of the support part has a curved concave shape extending entirely from the base part of the support part to a position where the Y axis coordinate value is 1.0 mm.

5. The intraocular lens according to claim 1, wherein the inner circumference side edge part of the support part has a curved concave shape with a roughly fixed radius of curvature set within a range of 0.3 to 0.7 mm at the base part of the support part extending across both sides sandwiching a contact point with the X axis.

6. The intraocular lens according to claim 1, wherein a width dimension in an X axis direction of the support part at a position where the Y coordinate value is the radius value of the optical part is larger than a width dimension in the X axis direction of the support part at a position where the Y coordinate value is 1.0 mm.

7. The intraocular lens according to claim 1, wherein the support part is positioned within a circumference of 7.5 mm in radius having the origin point of the orthogonal coordinate system as the center.

* * * * *